United States Patent [19]

Matsubara et al.

[11] 4,263,302

[45] Apr. 21, 1981

[54] QUINOLINECARBOXYLIC ACID SUBSTITUTED PENICILLINS AND PHARMACEUTICAL COMPOSITIONS CONTAINING THE SAME

[75] Inventors: Akira Matsubara, Yokohama; Hideaki Sakai, Fujisawa; Takuo Nakano, Yokohama; Toshio Suganuma, Mobara, all of Japan

[73] Assignee: Mitsui Toatsu Chemicals, Incorporated, Tokyo, Japan

[21] Appl. No.: 96,183

[22] Filed: Nov. 20, 1979

[30] Foreign Application Priority Data

Nov. 28, 1978 [JP] Japan .................... 53/146054

[51] Int. Cl.³ .................... A61K 31/47; C07D 499/70
[52] U.S. Cl. .................... 424/258; 260/239.1; 546/156
[58] Field of Search .................... 260/239.1; 424/258

[56] References Cited

U.S. PATENT DOCUMENTS

| 3,945,995 | 3/1976 | Yamada et al. | 260/239.1 |
| 3,951,955 | 4/1976 | Tobiki et al. | 260/239.1 |
| 4,008,220 | 2/1977 | Tobiki et al. | 260/239.1 |
| 4,190,581 | 2/1980 | Watanabe et al. | 260/239.1 |

FOREIGN PATENT DOCUMENTS 54-119484 9/1979 Japan .

OTHER PUBLICATIONS

Rolinson et al., "Antimicrobial Agents and Chemotherapy", pp. 609–613, (1967).
Williams et al., "Antimicrobial Agents and Chemotherapy", pp. 388–391, (1968).

*Primary Examiner*—Natalie Trousof
*Assistant Examiner*—Vera C. Clarke
*Attorney, Agent, or Firm*—Fisher, Christen & Sabol

[57] ABSTRACT

A penicillanic acid of the general formula

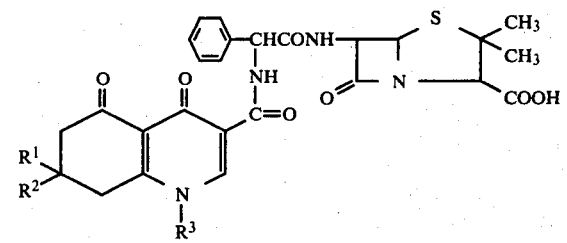

wherein $R^1$, $R^2$ and $R^3$ each represent a hydrogen atom or a lower alkyl group, provided that $R^1$, $R^2$ and $R^3$ do not simultaneously represent a hydrogen atom, or a biologically acceptable salt thereof.

5 Claims, No Drawings

QUINOLINECARBOXYLIC ACID SUBSTITUTED PENICILLINS AND PHARMACEUTICAL COMPOSITIONS CONTAINING THE SAME

This invention relates to novel penicillins. More specifically, this invention relates to penicillanic acids of the general formula

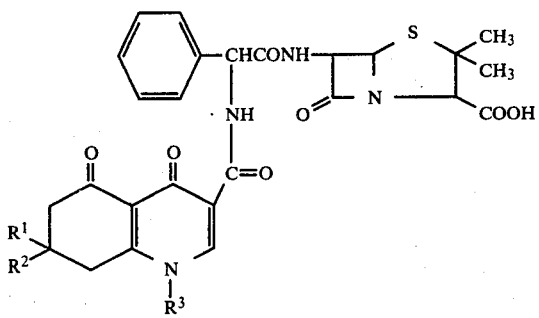

wherein $R^1$, $R^2$ and $R^3$ represent a hydrogen atom or a lower alkyl group, provided than $R^1$, $R^2$ and $R^3$ do not simultaneously represent a hydrogen atom, and the biologically acceptable salts thereof.

The number of infectious diseases caused by *Pseudomonas aeruginosa* has increased in recent years, and these diseases are frequently difficult to cure. It is desired therefore to develop drugs which are effective for infections by *Pseudomonas aeruginosa* with reduced side-effects.

It is known from "Antimicrobial Agents and Chemotherapy" --1967, 609 (1968) and ibid. --1968, 388 (1969), for example, that penicillin compounds such as carbenicillin (for example, carbenicillin sodium, disodium-α-carboxybenzyl penicillin, to be abbreviated CB-PC) have mainly been used for the treatment of infections by *Pseudomonas aeruginosa*. These compounds, however, have low activity on *Pseudomonas aeruginosa*, and must be administered in large quantities. Moreover, they are ineffective for *Pseudomonas aeruginosa*-induced infections of difficultly-curable nature.

It is an object of this invention therefore to provide drugs having high activity against *Pseudomonas aeruginosa*.

As a drug which meets this object, the present invention provides the penicillanic acids of general formula (1) and the biologically acceptable salts thereof.

Examples of the penicillanic acids of general formula (1) are 6-[D-(—)-α-(7,7-dimethyl-4,5-dioxo-1,4,5,6,7,8-hexahydroquinoline-3-carboxamido)phenylacetamido]-penicillanic acid and 6-[D-(—)-α-(1-ethyl-4,5-dioxo-1,4,5,6,7,8-hexahydroquinoline-3-carboxamido)-phenylacetamido]-penicillanic acid.

Examples of the biologically acceptable salts of the penicillanic acids are alkali metal salts such as lithium, sodium and potassium salts, alkaline earth metal salts such as calcium and magnesium salts, basic amino acid salts such as lysine, arginine and ornithine salts, and organic base salts such as triethylamine, benzylamine and procaine salts.

The penicillins of this invention have a broad range of antibacterial spectrum, and have strong antibacterial activity against Gram-negative bacteria, especially bacteria of the genus Pseudomonas. They are useful as therapeutic agents for infections.

The penicillin of this invention can be produced by reacting ampicillin of the formula

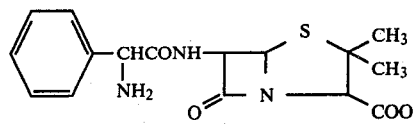

or its salt or its reactive derivative with a reactive derivative of a quinolinecarboxylic acid of the general formula

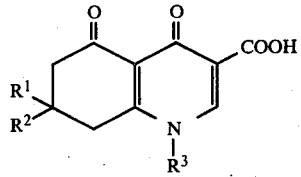

wherein $R^1$, $R^2$ and $R^3$ are as defined hereinabove.

The lower alkyl group in this application denotes an alkyl group having 1 to 5 carbon atoms.

Examples of the quinoline carboxylic acid of general formula (3) include 7,7-dimethyl-4,5-dioxo-1,4,5,6,7,8-hexahydroquinoline-3-carboxylic acid and 1-ethyl-4,5-dioxo-1,4,5,6,7,8-hexahydroquinoline-3-carboxylic acid.

The 1-ethyl-4,5-dioxo-1,4,5,6,7,8-hexahydroquinoline-3-carboxylic acid is a novel compound, and can be prepared by the method shown in Referential Example to be given hereinbelow.

The reactive derivatives of the quinoline carboxylic acids of general formula (3) include acid halides, mixed anhydrides and active esters.

The reaction of the ampicillin of formula (2) or its salt or its reactive derivative with the quinoline carboxylic acid of general formula (3) is carried out usually in a reaction solvent. Suitable reaction solvents include tetrahydrofuran, methylene chloride, chloroform, dioxane, acetic acid esters and dimethylformamide.

The following Referential Example and Synthesis Examples specifically illustrate the preparation of the penicillins of this invention.

REFERENTIAL EXAMPLE (1) Synthesis of ethyl 1-ethyl-4,5-dioxo-1,4,5,6,7,8-hexahydroquinoline-3-carboxylate:

By the method described in Japanese Patent Application No. 24956/1978, diethyl N-(3-oxo-1-cyclohexen-1-yl)-aminomethylenemalonate was prepared from 3-amino-2-cyclohexenone and diethyl ethoxymethylenemalonate. The product was cyclized under heat to form ethyl 4-hydroxy-5-oxo-5,6,7,8-tetrahydroquinonine-3-carboxylate, followed by hydrolysis. The resulting ethyl 4-hydroxy-5-oxo-5,6,7,8-tetrahydroquinoline-3-carboxylate (2.35 g) was suspended in 80 ml of dimethylformamide. The suspension was heated to 60° C., and 1.52 g of potassium carbonate and 1.54 g of ethyl iodide were added, and the mixture was stirred at 70° C. for 30 minutes. Further, 3.46 g of ethyl iodide was added, and the mixture was stirred for 1 hour. The insoluble matter was removed by filtration, and the mother liquor was concentrated to dryness. The product was extracted with chloroform, and the chloroform was distilled off. Methylene chloride was added to the residue, and the insoluble matter was collected by filtration. There was obtained 2.4 g of the captioned product as a light yellow powder. The nuclear magnetic resonance spectrum (DMSO-d$_6$, 60 MC, TMS) had signals at δ1.2–1.5 (6H, m), 1.8–3.3 (6H, m), 4.0–4.5 (4H, m), and 8.4 (1H, s).

(2) Synthesis of 1-ethyl-4,5-dioxo-1,4,5,6,7,8-hexahydroquinoline-3-carboxylic acid:

Sodium hydroxide (1.6 g) was dissolved in 30 ml of water, and 2 g of ethyl 1-ethyl-4,5-dioxo-1,4,5,6,7,8-hexahydroquinoline-3-carboxylate was added, and the mixture was stirred at 90° C. for 2 hours. The insoluble matter was removed, and the filtrate was adjusted to pH 1 with dilute hydrochloric acid under ice cooling. The crystals that precipitated were collected by filtration to afford 0.72 g of the captioned product. The product had a melting point of 212° to 214° C. (uncorrected). The infrared absorption spectrum (KBr tablet method) of the product had maximum absorptions at 3460, 2960, 1740, 1710, 1640 and 1495 cm$^{-1}$. The nuclear magnetic resonance spectrum (CF$_3$COOH, 60 Mc, TMS) had signals at δ1.70 (3H, t, J=7.5 Hz), 2.2–2.75 (2H, m), 2.8–3.2 (2H, m), 3.3–3.65 (2H, m), 4.64 (2H, q, J=7.5 Hz) and 9.30 (1H, s).

SYNTHESIS EXAMPLE 1

Synthesis of 6-[D-(−)-α-(7,7-dimethyl-4,5-dioxo-1,4,5,6,7,8-hexahydroquinoline-3-carboxamido)phenylacetamido]-penicillanic acid In a mixture of 20 ml of methylene chloride and 1.11 g of triethylamine was dissolved 1.29 g of 7,7-dimethyl-4,5-dioxo-1,4,5,6,7,8-hexahydroquinoline-3-carboxylic acid. The solution was cooled to −15° C. to −10° C., and a solution of 1.19 g of ethyl chloroformate in 5 ml of methylene chloride was added dropwise. The mixture was stirred for 30 minutes at −15° C. to −10° C., and then a solution of 2.02 g of ampicillin trihydrate in a mixture of 15 ml of methylene chloride, 5 ml of isopropyl alcohol and 1.0 g of triethylamine was added. The mixture was stirred at −10° C. to 0° C. for 30 minutes, and the solvent was distilled off. Water (50 ml) and 1.4 g of potassium carbonate were added to the residue, and the mixture was stirred at room temperature for 15 minutes. The pH of the mixture was adjusted to 2 with 40% phosphoric acid, and the crystals that precipitated were collected by filtration. The filtrate was saturated with sodium chloride, and the crystals that precipitated were collected by filtration. The crystals were purified by using a column packed with silica gel to form 0.45 g of the captioned product as a while powder.

The infrared absorption specturm (KBr tablet method) of the product had maximum absorptions at 3250, 3080, 2980, 1790, 1760, 1700, 1625, 1540, 1500, 1340, 1210 and 1080 cm$^{-1}$.

The nuclear magnetic resonance spectrum (DMSO-d$_6$, 60 Mc, TMS) of the product had signals at δ1.03 (6H, br. s), 1.45 (3H, s), 1.59 (3H, s), 2.1–3.1 (4H, m), 4.20 (1H, s), 5.3–5.7 (2H, m), 5.92 (1H, d, J=8 Hz), 7.1–7.7 (5H, m), 8.40 (1H, s), 9.26 (H, d, J=8 Hz) and 11.09 (1H, d, J=8 Hz).

SYNTHESIS EXAMPLE 2

Synthesis of 6-[D-(−)-α-(1-ethyl-4,5-dioxo-1,4,5,6,7,8-hexahydroquinoline-3-carboxamodo)phenylacetamido]-penicillanic acid In a mixture of 15 ml of methylene chloride, 6 ml of dimethylformamide and 0.52 g of triethylamine was dissolved 0.60 g of 1-ethyl-4,5-dioxo-1,4,5,6,7,8-hexahydroquinoline-3-carboxylic acid. The solution was cooled to −15° C. to −12° C., and a solution of 0.3 g of ethyl chloroformate in 5 ml of methylene chloride was added dropwise. The mixture was stirred at −15° C. to −12° C. for 10 minutes, and then a solution of 1.13 g of ampicillin trihydrate in 10 ml of methylene chloride, 5 ml of isopropyl alcohol and 0.52 g of triethylamine was added. The mixture was stirred at −10° C. to −12° C. for 1.5 hours, and the solvent was distilled off. The residue was dissolved in water, and its pH was adjusted to 2 with 40% phosphoric acid. The crystals that precipitated were purified by using a column filled with silica gel to afford 0.81 g of the captioned product as a white powder.

The infrared absorption spectrum (KBr tablet method) of the product had maximum absorptions at 1790, 1755, 1700, 1630, 1540, 1500, 1480, 1345, 1230, 1110 and 820 cm$^{-1}$.

The nuclear magnetic resonance spectrum (DMSO-d$_6$, 60 Mc, TMS) of this product had signals at δ1.1–1.7 (9H, m), 1.8–3.3 (6H, m), 3.8–4.5 (2H, m), 4.19 (1H, s), 5.3–6.4 (5H, m), 7.1–7.6 (5H, m), 8.45 (1H, s), 9.22 (1H, d, J=8 Hz), and 11.10 (1H, d, J=8 Hz).

The antibacterial activity of the penicillin of this invention is shown in the following test example.

TEST EXAMPLE

The antibacterial activity was tested by the minimum growth inhibitory concentration method (MIC method).

A commercially available heart infusion agar medium (to be abbreviated HIA medium) was used as an assay medium, and a commercially available trypto-soy bouillon medium (to be abbreviated TSB) was used as a medium for the growth of test bacterial strains.

The test compound was diluted with the melted HIA medium to 100 μg/ml as a maximum concentration, and then serially diluted doubly. The dilutions were poured into sterilized Petri dishes respectively and allowed to cool and solidify to prepare plates containing the test compound.

As a control, carbenicillin sodium (CB-PC) was used.

The test strain was cultivated in the TBS medium at 37° C. for 18 hours, and the culture broth was diluted with a freshly prepared TBS medium to 50 to 500 times, and one platinum loopful of the dilution was inoculated in each of the plates containing the test compound. The plate was incubated at 37° C. for 18 hours. The state of growth of the strain on the plate was observed, and the minimum growth inhibitory concentration (MIC) of the compound was determined. The results are shown in Table 1.

It is seen from Table 1 that the compounds of this invention have a broad range of antibacterial spectrum, and their antibacterial activities are of high level. They showed especially strong antibacterial activity against *Pseudomonas aeruginosa*.

TABLE 1

| Test compounds Test bacterial strains | Minimum growth inhibitory concentration (μg/ml) | | |
| --- | --- | --- | --- |
| | Compound of Synthesis Example 1 | Compound of Synthesis Example 2 | CB—PC |
| *Staphylococcus aureus* (FDA 209P) | 1.56 | 1.56 | 1.56 |
| *Staphylococcus aureus* (Y-8) | 6.25 | 6.25 | 6.25 |
| *Escherichia coli* (K-12) | 0.78 | 3.13 | 6.25 |
| *Klebsiella pneumoniae* (ATCC 10031) | 12.5 | 25 | >100 |
| *Shigella flexneri* (K-A) | 0.39 | 0.78 | 1.56 |
| Salmonellaenteritidis (KB-21) | 0.39 | 0.78 | 1.56 |
| *Proteus vulgaris* (OX-19) | 1.56 | 3.13 | 3.13 |
| *Pseudomonas aeruginosa* (IFO-3901) | 6.25 | 6.25 | 100 |
| *Pseudomonas aeruginosa* (395) | 1.56 | 3.13 | 25 |
| *Serratia marcescens* (S-33) | 3.13 | 3.13 | 3.13 |
| *Enterobacter aerogenes* (IFO-3320) | 0.78 | 1.56 | 1.56 |

As is apparent from the foregoing description, the penicillins of this invention have very good antibacterial activity, and are useful as antibacterial agents. They can be used not only for the treatment and prevention of bacterial infections of mammals including humans, and also as disinfectants. In administration to humans, the dose of the penicillin of this invention is 100 to 1500 mg, preferably 250 to 1000 mg per administration. Preferably, it is administered several times a day.

Pharmaceuticals containing the compound of this invention as an active ingredient may be in the form of solids such as tablets, capsules and powders, or liquids such as injections or suspensions. Additives usually employed in the art, such as vehicles, stabilizers and wetting agents, may be used.

What we claim is:

1. A penicillanic acid of the general formula

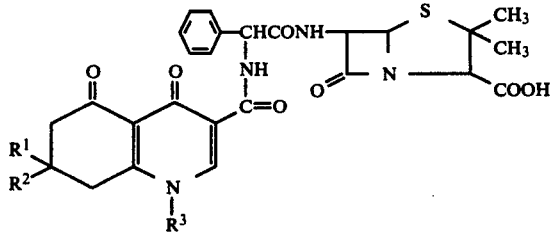

wherein $R^1$, $R^2$ and $R^3$ each represent a hydrogen atom or a lower alkyl group, provided that $R^1$, $R^2$ and $R^3$ do not simultaneously represent a hydrogen atom, or a biologically acceptable salt thereof.

2. The salt of claim 1 which is an alkali metal salt, alkaline earth metal salt, basic amino acid salt or organic base salt of the penicillanic acid.

3. Penicillanic acid of the formula

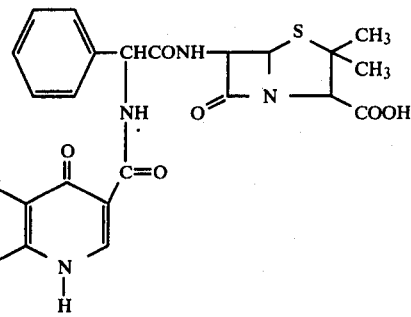

or a biologically acceptable salt thereof.

4. Penicillanic acid of the formula

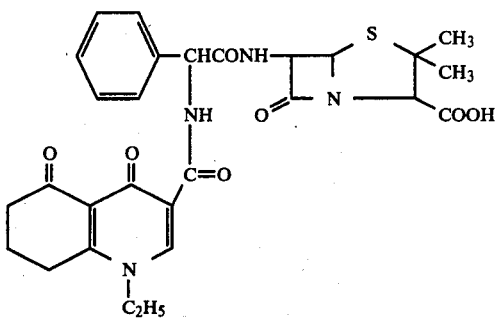

or a biologically acceptable salt thereof.

5. An antibacterial composition comprising a pharmaceutically effective amount of a penicillanic acid of the general formula

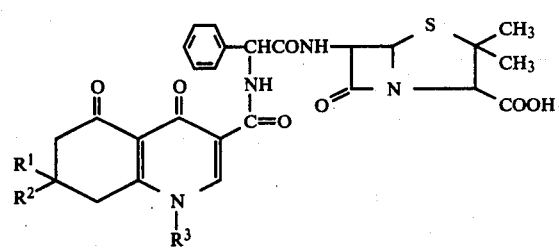

wherein $R^1$, $R^2$ and $R^3$ each represent a hydrogen atom or a lower alkyl group, provided that $R^1$, $R^2$ and $R^3$ do not simultaneously represent a hydrogen atom, or a biologically acceptable salt thereof as an active ingredient in a pharmaceutical carrier.